(12) United States Patent
Cig et al.

(10) Patent No.: US 10,358,917 B2
(45) Date of Patent: Jul. 23, 2019

(54) GENERATING RELATIVE PERMEABILITIES AND CAPILLARY PRESSURES

(71) Applicant: Schlumberger Technology Corporation, Sugar Land, TX (US)

(72) Inventors: Koksal Cig, Izmir (TR); Cosan Ayan, Istanbul (TR); Morten Kristensen, Auning (DK)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 831 days.

(21) Appl. No.: 14/741,913

(22) Filed: Jun. 17, 2015

(65) Prior Publication Data
US 2015/0369957 A1     Dec. 24, 2015

Related U.S. Application Data

(60) Provisional application No. 62/013,797, filed on Jun. 18, 2014.

(51) Int. Cl.
*G01V 8/02*     (2006.01)
*E21B 49/08*   (2006.01)
(Continued)

(52) U.S. Cl.
CPC .............. *E21B 49/08* (2013.01); *E21B 49/00* (2013.01); *E21B 49/088* (2013.01); *E21B 49/10* (2013.01); *G01N 15/0826* (2013.01)

(58) Field of Classification Search
CPC ........ E21B 49/00; E21B 49/08; E21B 49/088; E21B 49/10; G01N 15/0826
See application file for complete search history.

(56) References Cited

U.S. PATENT DOCUMENTS 5,335,542 A     8/1994 Ramakrishnan et al.

OTHER PUBLICATIONS

Angeles et al. "Efficient and Accurate Estimation of Permeability and Permeability Anisotropy From Straddle-Packer Formation Tester Measurements Using the Physics of Two-Phase Immiscible Flow and Invasion," SPE 95897, prepared for presentation at the 2005 SPE Annual Technical Conference and Exhibition held in Dallas, Texas, U.S.A., Oct. 9-12, 2005, pp. 1-19.

(Continued)

*Primary Examiner* — Sujoy K Kundu
*Assistant Examiner* — L. Anderson
(74) *Attorney, Agent, or Firm* — Michael Dae

(57) ABSTRACT

An apparatus is operated to obtain a model predicting data associated with a theoretical sampling operation to be performed by a downhole sampling tool, including predicted water-cut and pressure data relative to time elapsed during the theoretical sampling operation. The model predicts the water-cut and pressure data based on estimated relative permeability and capillary pressure related to different constituents of fluid theoretically obtained from a subterranean formation by the downhole sampling tool during the theoretical sampling operation. An actual sampling operation is performed with the downhole sampling tool to actually obtain fluid and data associated with the actually obtained fluid, including actual water-cut and drawdown pressure data. The apparatus is then operated to update the model utilizing the actual data water-cut and drawdown pressure data, thus obtaining actual relative permeability and capillary pressure data.

20 Claims, 6 Drawing Sheets

(51) Int. Cl.
*E21B 49/00* (2006.01)
*E21B 49/10* (2006.01)
*G01N 15/08* (2006.01)

(56) References Cited

OTHER PUBLICATIONS

Akram et al. A Model to Predict Wireline Formation Tester Sample Contamination, SPE 48959, SPE ATCE, New Orleans, Louisiana, Sep. 27-30, 1998.
Ansari et al. "A Comprehensive Mechanistic Model for Upward Two-Phase Flow in Wellbores," SPE Production & Facilities 9, No. 2, pp. 143-152, May 1994.
Cig et al. "Improvements of Sampling and Pressure Measurements with a New Wireline Formation Tester Module in Carbonate Reservoirs," IPTC 17579, IPTC Doha, Qatar, Jan. 20-22, 2014, pp. 1-8.
Hagedorn et al. "Experimental Study of Pressure Gradients Occurring During Continuous Two-Phase Flow in Small-Diameter Vertical Conduits," Journal of Petroleum Technology, Apr. 17, 1965, No. 4, pp. 475-484.
Hasan et al. "A Simplified Model for Oil/Water Flow in Vertical and Deviated Wellbores," SPE 54131, SPE Production & Facilities, 14, 1999, No. 1, pp. 56-62, also presented at SPE ATCE, New Orleans, Louisiana, USA, Sep. 27-30, 1998.
Salazar et al. "Automatic Estimation of Permeability from Array Induction Measurements: Applications to Field Data," SPWLA 46th Annual Logging Symposium, Jun. 26-29, 2005, pp. 1-15.
Shi, et al. "Drift-Flux Modeling of Multiphase Flow in Wellbores," SPE 84228, SPE ATCE, Denver, Colorado, U.S.A., Oct. 5-8, 2003, pp. 1-11.
Shi et al. Drift-Flux Parameters for Three-Phase Steady-State Flow in Wellbores, SPE 89836, Society of Petroleum Engineers Journal,10, 2005, No. 2, pp. 1-10; also presented at the SPE ATCE, Houston, Texas, USA, Sep. 26-29, 2004.
Wu et al. "A New Inversion Technique Determines In-situ Relative Permeabilities and Capillary Pressure Parameters From Pumpout Wireline Formation Tester Data," SPWLA 44th Annual Logging Symposium, Galveston, Texas, USA, Jun. 22-25, 2003, pp. 1-14.
Zazovsky "Monitoring and Prediction of Cleanup Production During Sampling," SPE 112409, SPE International Symposium and Exhibition on Formation Damage Control, Lafayette, Louisiana, USA, Feb. 13-15, 2008, pp. 1-10.
Zeybek et al. "Estimating Multiphase Flow Properties Using Pressure and Flowline Water-Cut data from Dual Packer Formation tester Interval tests and Openhole Array Resistivity Measurements," SPE 71568, SPE ATCE, New Orleans, Louisiana, USA, Sep. 30-Oct. 3, 2001, pp. 1-8.
Zeybek et al. "Estimating Multiphase-Flow Properties from Dual-Packer Formation-Tester Interval Tests and Openhole Array Resistivity Measurements," SPE 87474, Feb. 2004, SPE Reservoir Evaluation & Engineering, pp. 40-46.
Brooks, R.H. and Corey A.T.: 'Hydraulic Properties of Porous Media', Colorado State U., Fort Collins, Colorado, Hydrology Papers, Paper No. 5, Mar. 1964 (37 pages).
Frandsen P.E. , Jonasson K., Nielsen H.B., Tingleff O.: 'Unconstrained Optimization', Department of Mathematical Modeling, Technical University of Denmark, 1999 (40 pages).
Harmathy, T. Z.: 'Velocity of Large Drops and Bubbles in Media of Infinite and Restricted Extent', American Institute of Chemical Engineering Journal, 6, 1960, No. 2, p. 281-288.
Rinnooy Kan A.H.G., Boender C.G.E., Tinmer G.T.: 'A Stochastic Approach to Global Optimization', WP1602-84, Oct. 1984 (34 pages).
Lomeland F., Ebeltoft E., Thomas1 W. H.: 'A New Versatile Relative Permeability Correlation', International Symposium of the Society of Core Analysts, Toronto, Canada, Aug. 21-25, 2005 (12 pages).
Zimmerman T., MacInnis J., Hoppe J., Pop J. and Long T.: 'Application of Emerging Wireline Formation Testing Technologies', OSEA-90081, 8th Offshore South East Asia Conference, Singapore, Dec. 4-7, 1990 (14 pages).
Zuber, N. and Findlay, J. A. : 'Average Volumetric Concentration in Two-Phase Flow Systems', Transactions of ASME, Ser. C, Journal of Heat Transfer, 87, 1965, No. 4, p. 453-468.

GENERATING RELATIVE PERMEABILITIES AND CAPILLARY PRESSURES

CROSS-REFERENCE TO RELATED APPLICATIONS

This application claims priority to and the benefit of U.S. Provisional Application No. 62/013,797, entitled "Generating Relative Permeabilities and Capillary Pressures," filed Jun. 18, 2014, the entire disclosure of which is hereby incorporated herein by reference.

BACKGROUND OF THE DISCLOSURE

As a wellbore is drilled into a subterranean formation, the formation near the wellbore is exposed to drilling fluid ("mud") filtrate invasion. When such drilling operations utilize a water-based mud ("WBM"), for example, the invasion displaces oil in the vicinity of the wellbore because the mud filtrate and the oil in the formation are immiscible. A similar situation exists when oil-based mud (OBM) is utilized to form a wellbore in a formation containing non-oil formation fluids, such as water or a combination of water and gas.

However, existing in-situ formation fluid testing techniques often rely on algorithms that assume the mud and formation fluids are miscible, and may therefore provide inaccurate results with regard to the various parameters of the formation fluid being investigated. Alternatively, a core sample may be removed from the formation and transported away from the wellsite for laboratory testing that can account for the immiscible nature of the filtrate and formation fluids. However, several weeks or months may elapse before the lab results are available.

SUMMARY OF THE DISCLOSURE

This summary is provided to introduce a selection of concepts that are further described below in the detailed description. This summary is not intended to identify indispensable features of the claimed subject matter, nor is it intended for use as an aid in limiting the scope of the claimed subject matter.

The present disclosure introduces a method that includes operating an apparatus to obtain a model predicting data associated with a theoretical sampling operation to be performed by a downhole sampling tool. The predicted data includes predicted water-cut and drawdown pressure data relative to time elapsed during the theoretical sampling operation. The model predicts the time-based water-cut and drawdown pressure data based on estimated relative permeability and capillary pressure related to different constituents of fluid theoretically obtained from a subterranean formation by the downhole sampling tool during the theoretical sampling operation. The method also includes performing an actual sampling operation with the downhole sampling tool to actually obtain fluid from the subterranean formation and actual data associated with the actually obtained fluid. The actual data comprises actual water-cut and drawdown pressure data relative to time elapsed during the actual sampling operation. The method also includes operating the apparatus to update the model utilizing the actual data water-cut and drawdown pressure data, thus obtaining actual relative permeability and capillary pressure related to different constituents of the actual fluid obtained during the actual sampling operation.

The present disclosure also introduces a system that includes a downhole sampling tool operable within a wellbore extending from a wellsite surface into a subterranean formation. The downhole sampling tool is operable to perform an actual sampling operation to actually obtain fluid from the subterranean formation and actual data associated with the actually obtained fluid. The actual data includes actual water-cut and drawdown pressure data relative to time elapsed during the actual sampling operation. The system also includes an apparatus operable to update a model utilizing the actual data water-cut and drawdown pressure data. The model predicts data associated with a theoretical sampling operation to be performed by the downhole sampling tool. The predicted data includes predicted water-cut and drawdown pressure data, relative to time elapsed during the theoretical sampling operation, based on estimated relative permeability and capillary pressure related to different constituents of fluid theoretically obtained from the subterranean formation by the downhole sampling tool during the theoretical sampling operation. The apparatus is operable to update the model by iteratively adjusting the estimated relative permeability and capillary pressure until the predicted water-cut and drawdown pressure data substantially matches the actual water-cut and drawdown pressure data, thus obtaining actual relative permeability and capillary pressure related to different constituents of the actual fluid obtained during the actual sampling operation.

The present disclosure also introduces a method that includes operating an apparatus to obtain a model predicting data associated with a theoretical sampling operation to be performed by a downhole sampling tool. The predicted data includes predicted water-cut and drawdown pressure data relative to time elapsed during the theoretical sampling operation. The model predicts the time-based water-cut and drawdown pressure data based on estimated relative permeability and capillary pressure related to different constituents of fluid theoretically obtained from a subterranean formation by the downhole sampling tool during the theoretical sampling operation. The method also includes performing an actual sampling operation with the downhole sampling tool to actually obtain fluid from the subterranean formation. The model is a drift-flux model if the actual sampling operation utilizes a dual-packer module of the downhole sampling tool to actually obtain fluid from the subterranean formation. The model is a homogenous model if the actual sampling operation utilizes a probe of the downhole sampling tool to actually obtain fluid from the subterranean formation. Either the dual-packer module or the probe is utilized to actually obtain fluid from the subterranean formation. The method also includes obtaining actual data associated with the actually obtained fluid during the actual sampling operation. The actual data includes actual water-cut and drawdown pressure data relative to time elapsed during the actual sampling operation. The method also includes operating the apparatus to update the model by iteratively adjusting the estimated relative permeability and capillary pressure until the predicted water-cut and drawdown pressure data substantially matches the actual water-cut and drawdown pressure data, thus obtaining actual relative permeability and capillary pressure related to different constituents of the actual fluid obtained during the actual sampling operation.

These and additional aspects of the present disclosure are set forth in the description that follows, and/or may be learned by a person having ordinary skill in the art by reading the materials herein and/or practicing the principles described herein. At least some aspects of the present disclosure may be achieved via means recited in the attached claims.

BRIEF DESCRIPTION OF THE DRAWINGS

The present disclosure is best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion.

DETAILED DESCRIPTION

Figure 1:
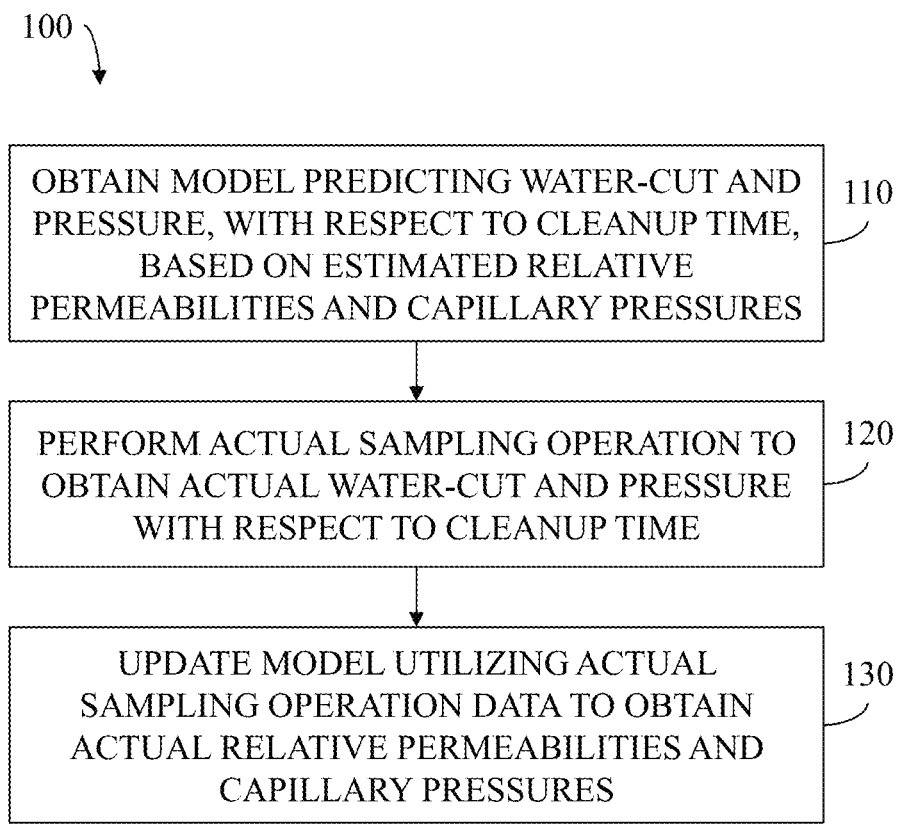
FIG. 1 is a flow-chart diagram of at least a portion of an example implementation of a method according to one or more aspects of the present disclosure.

It is to be understood that the following disclosure provides many different embodiments, or examples, for implementing different features of various embodiments. Specific examples of components and arrangements are described below to simplify the present disclosure. These are, of course, merely examples and are not intended to be limiting. In addition, the present disclosure may repeat reference numerals and/or letters in the various examples. This repetition is for simplicity and clarity, and does not in itself dictate a relationship between the various embodiments and/or configurations discussed. Moreover, the formation of a first feature over or on a second feature in the description that follows may include embodiments in which the first and second features are formed in direct contact, and may also include embodiments in which additional features may be formed interposing the first and second features, such that the first and second features may not be in direct contact.

In the context of the present disclosure, the term "cleanup" pertains to operating a downhole sampling tool to pump fluid out of a subterranean formation after contamination is introduced into the subterranean formation during a drilling operation. The pumped fluid initially comprises substantially more mud filtrate than native formation fluid, and continued pumping ultimately results in obtaining fluid that has a sufficiently low proportion of mud filtrate (e.g., about five or ten percent, by volume) in the native formation fluid. The term "sampling" includes storing a sample of such sufficiently "clean" fluid (oil, water, and/or gas) obtained from the subterranean formation in an internal chamber of the downhole sampling tool. The phrase "sampling operation" includes both a cleanup phase and a sampling phase.

Data obtained via operation of one or more downhole fluid analyzers or sensors of the downhole sampling tool (and/or other tools in the tool string) during the sampling operation may include, be determined from, or be utilized to determine drawdown pressure (created by the downhole sampling tool to urge fluid from the formation into the downhole sampling tool), water-cut (the volumetric proportion of water in the fluid obtained from the formation by the downhole sampling tool), viscosity, density, and gas-oil-ratio (GOR), among others.

FIG. 1 is a flow-chart diagram of at least a portion of a method (100) according to one or more aspects of the present disclosure. The method (100) comprises operating (110) an apparatus to obtain a model predicting data associated with a theoretical sampling operation to be performed by a downhole sampling tool. The apparatus operated (110) to obtain the model may have one or more aspects in common with at least a portion of the apparatus described below. For example, the apparatus operated (110) to obtain the model may be, comprise, or form at least a portion of the processing system 600 shown in FIG. 7, whether located at the wellsite (such as within the surface equipment 315 shown in FIG. 4 and/or the surface equipment 521 shown in FIG. 6) or remote from the wellsite.

The predicted data comprises predicted water-cut and drawdown pressure data relative to time elapsed during the theoretical sampling operation. The model predicts the time-based water-cut and drawdown pressure data based on estimated relative permeability and capillary pressure related to different constituents of fluid theoretically obtained from a subterranean formation by the downhole sampling tool during the theoretical sampling operation. The model may be or comprise a numerical simulation comprising and/or otherwise utilizing radial, block centered, Cartesian, structured, and/or unstructured gridding techniques, among other possible examples. The model simulates timed-based changes in water-cut and pressure during cleanup of near-wellbore mud filtrate invasion based on the estimated relative permeabilities and capillary pressures. The model may also comprise relative permeability end points, saturation end points, and/or capillary pressure parameters, such as entry, minimum, and/or maximum pressures. Damage skin may also be utilized as a parameter, and may be useful as an optimization input due, for example, to its effect on pressure drawdown in the near-wellbore region. The data utilized to obtain the initial model may also be obtained from open-hole logs, reservoir properties, and/or other sources.

An actual sampling operation is then performed (120) with the downhole sampling tool to actually obtain fluid from the subterranean formation, as well as to obtain actual data associated with the actually obtained fluid. The actual sampling operation is performed with the downhole sampling tool disposed in a wellbore extending into the subterranean formation, and the actual data comprises actual water-cut and drawdown pressure data relative to time elapsed during the actual sampling operation. The actual data may also comprise viscosity, density, and/or GOR of the actually obtained fluid, among other example fluid parameters.

Performing (120) the actual sampling operation may comprise isolating an interval of the wellbore by extending two packers of the downhole sampling tool into substantially sealing contact with a perimeter of the wellbore, and then reducing pressure within the isolated wellbore interval to draw fluid from the subterranean formation into the isolated wellbore interval. In such implementations, the model is a drift-flux model that includes geometric data related to a dimension or volume of the isolated wellbore interval. The drift-flux model may also account for a time delay associated with accumulation of the actually obtained fluid in the isolated wellbore interval before the actually obtained fluid is drawn into the downhole sampling tool.

Performing (120) the actual sampling operation may instead comprise establishing substantially sealing contact between an inlet of a probe of the downhole sampling tool and a location on a perimeter of the wellbore, and then reducing pressure within the probe inlet to draw fluid from the subterranean formation into the downhole sampling tool. In such implementations, the model may be a drift-flux model or a homogenous model having inputs that include geometric data related to a dimension or volume of the probe inlet.

The apparatus previously operated (110) to obtain the model is then operated (130) to update the model utilizing the actual data water-cut and drawdown pressure data, thus obtaining actual relative permeability and capillary pressure related to different constituents of the actual fluid obtained during the actual sampling operation.

Operating (130) the apparatus to update the model may comprise iteratively adjusting the estimated relative permeability and capillary pressure until the predicted water-cut and drawdown pressure data substantially matches the actual water-cut and drawdown pressure data. For example, updating the model may utilize gradient, deterministic, stochastic, Monte Carlo, and/or other optimization techniques. Such optimization techniques permit the relative permeability and capillary pressure parameters to be inverted substantially concurrently, thus utilizing the relative permeability and capillary pressure estimates with the actual water-cut and pressure data to reveal the actual relative permeability and capillary pressure values.

The fluid theoretically obtained during the theoretical sampling operation and the fluid actually obtained during the actual sampling operation comprises two immiscible fluids. For example, the two immiscible fluids may comprise a first fluid substantially comprising water and a second fluid substantially comprising hydrocarbons. That is, in such implementations, the wellbore may have been formed in the subterranean formation by a drilling operation that utilized water-based drilling fluid, such that during early stages of the theoretical and actual sampling operations, the theoretically and actually obtained fluids comprise substantially more water than hydrocarbons, whereas during late stages of the theoretical and actual sampling operations, the theoretically and actually obtained fluids comprise substantially more hydrocarbons than water.

In other implementations, the two immiscible fluids may comprise a first fluid substantially comprising oil and a second fluid substantially comprising water. In such implementations, the wellbore may have been formed in the subterranean formation by a drilling operation that utilized oil-based drilling fluid, such that during early stages of the theoretical and actual sampling operations, the theoretically and actually obtained fluids comprise substantially more oil than water, whereas during late stages of the theoretical and actual sampling operations, the theoretically and actually obtained fluids comprise substantially more of water than oil. In implementations in which one of the first and second immiscible fluids comprises water, that fluid may also comprise gas.

As mentioned above, laboratory core analysis is conventionally utilized to measure relative permeabilities and capillary pressures. However, such core analysis may involve extended waiting periods due to, for example, the laborious workflow characteristic of core analysis. However, the present disclosure introduces one or more substantially automated methodologies that may reduce such delay and/or obtain the relative permeabilities and capillary pressures without the complexity and extended waiting periods inherent to laboratory core analysis.

Past commentators have also studied immiscible contamination cleanup modeling with homogenous flow models. However, such models did not account for the different geometries of the various downhole sampling tools able to perform such cleanup, such as the different volumes, shapes, and/or other parameters of the various inlets, flowlines, modules, and other features, as introduced in the present disclosure. The present disclosure introduces the utilization of a drift-flux flow model to account for the different geometries of individual downhole sampling tools. The drift-flux model may be utilized if the downhole sampling tool utilizes a probe to obtain fluid from the formation, and provides substantially more accurate results if the downhole sampling tool utilizes a dual-packer device to obtain the fluid from the formation.

That is, homogeneous flow models assume that fluid properties can be represented by mixture properties, and that single-phase flow techniques can be applied to the mixture. However, the present disclosure introduces a drift-flux flow model that modifies the homogenous flow model to, for example, account for slip between the different phases of the constituents of the fluid obtained from the formation. Such approach may utilize one or more empirical parameters. "Slip" refers to the different velocities of the fluids that arrive at the downhole sampling tool. Due to slip, fluids may accumulate or segregate in the inlet and/or dual-packer interval, depending on the associated volume, velocity, flow profile, and/or other parameters.

Cleanup modeling utilizing a drift-flux model according to one or more aspects of the present disclosure may account for different inlet types. Inlet types utilized according to aspects of the present disclosure may include a dual-packer arrangement, such as the dual-packer module 55 described below with respect to FIG. 2, or a probe arrangement, such as the probe 50 described below with respect to FIG. 2. Cleanup modeling with a dual-packer module implemented with a drift-flux flow model may account for segregation of fluids in the wellbore interval isolated by the dual packers, and may depict realistic fluid behavior and/or measurements of pressures, fluid rates, and/or water-cuts, which may then be utilized for history matching to acquire actual relative permeabilities and capillary pressures.

One or more aspects of the present disclosure may thus permit increased accuracy of the actual relative permeability and capillary pressure values. The increased accuracy may be attributable to, for example, utilizing accurate geometry and volume definitions of the downhole sampling tool, and/or utilizing drift-flux flow modeling instead of homogenous flow modeling based on the geometry and type of the downhole sampling tool utilized during the cleanup operation.

One or more aspects of the present disclosure may also permit faster or real-time results. That is, implementations introduced herein may provide results during or after the actual cleanup operation, in contrast to conventional, time-intensive laboratory analyses.

Figure 2:
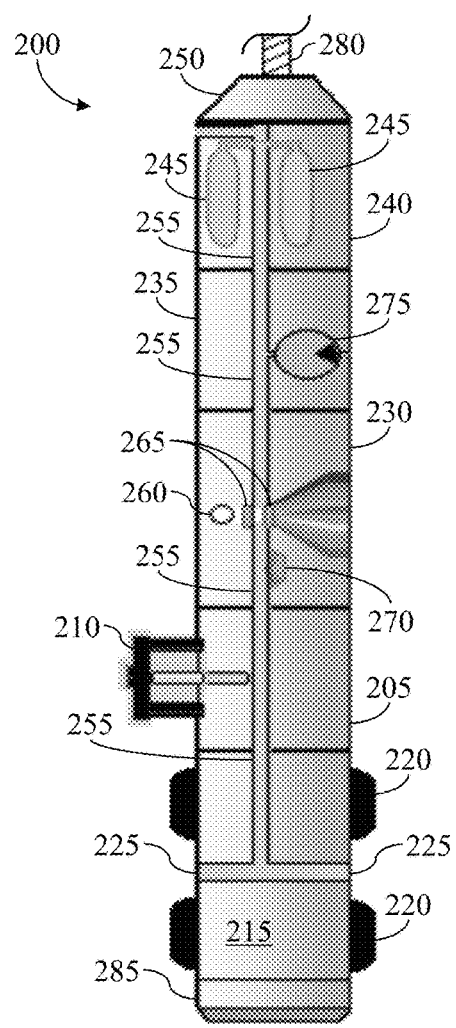
FIG. 2 is a schematic view of at least a portion of an example implementation of apparatus according to one or more aspects of the present disclosure.

FIG. 2 is a schematic view of at least a portion of an example implementation of a downhole sampling tool 200 according to one or more aspects of the present disclosure. The downhole sampling tool 200 may comprise a probe module 205 comprising one or more probes 210, a dual-packer module 215 comprising two packers 220 and at least one port 225, a fluid analyzer module 230, and a pumpout module 235. The downhole sampling tool 200 may also comprise a sample module 240, comprising one or more detachable sample bottles and/or other sample chambers 245, and a conveyance terminal 250. However, other implementations of downhole sampling tools are also within the scope of the present disclosure.

The probe 210 may be hydraulically or otherwise extendable from the downhole sampling tool 200 into contact with a sidewall of the wellbore, including for sealing contact therewith to establish fluid communication between the formation (penetrated by the wellbore) and one or more internal flow lines 255 spanning a substantial portion of the length of the downhole sampling tool 200. The probe 210 may also or instead be urged into contact with the wellbore sidewall via operation of one or more back-up pistons and/or apparatus (not shown) operable to urge the downhole sampling tool 200 towards the wellbore sidewall.

The dual-packer module 215 may comprise two (or more) single packer modules, tools, and/or apparatus, and/or form a portion of multi-packer module, tool, and/or apparatus having more than two packers 220 (such as a quad-packer apparatus comprising four packers). The packers 220 are independently and/or collectively operable to isolate a portion of the annulus formed between the wellbore sidewall and the outer profile of the downhole sampling tool 200, such as by mechanical, hydraulic, pneumatic, and/or other means for expanding and/or otherwise extending the packers 220 into contact with the wellbore sidewall. The dual-packer module 215 may be, form, comprise, and/or be replaced by a tool and/or module comprising more or less than two packers, a radial probe, more or less than two ports 225, and/or other apparatus, components, and/or features.

The fluid analyzer module 230 may be operable to determine, estimate, and/or otherwise obtain various parameters and/or other information pertaining to the fluid flowing in the flowline 255. For example, the fluid analyzer module 230 is depicted as having spectrometry capabilities, thus comprising a laser and/or other light source 260 and one or more detectors 265, wherein the light source 260 and detectors 265 are disposed on opposite sides of the flowline 255 through which the fluid obtained from the formation flows. However, the fluid analyzer module 230 may also or instead comprise one or more other sensors 270 operable in determining various other parameters pertaining to the fluid flow in the flowline 255, such as pressure, water-cut, temperature, density, viscosity, conductivity, GOR, and/or myriad others.

The detectors 265 may comprise one or more detector elements that may each be operable to measure the amount of light transmitted at a certain wavelength. For example, the detector elements may detect the light transmitted from the visible to near-infrared within a range of one, five, ten, twenty, or more different wavelengths ranging between about 400 nm and about 2200 nm. However, other numbers of wavelengths (corresponding to the number of detector elements) and other ranges of wavelengths are also within the scope of the present disclosure. For example, optical characteristics of the fluid obtained from the formation may be detected at a range of wavelengths, such as the near infrared (NIR) wavelength range of approximately 800-2500 nm, 1500-2050 nm, or 1600-1800 nm. Estimations of fluid properties according to one or more aspects of the present disclosure may utilize optical data collected at a single wavelength, at multiple wavelengths, a range of wavelengths, and/or multiple ranges of wavelengths.

The spectrometer may measure one or more optical characteristics of the fluid flowing through the flowline 255 and output optical spectra and/or other data representative of the detected optical characteristics. The optical characteristics may include optical density (OD) of the fluid at each of the detected wavelengths and/or wavelength ranges. The OD is a logarithmic measurement relating the intensity of light emitted from the light source 260 to the intensity of light detected by the detectors 265 at a certain wavelength or range of wavelengths. The OD data may be indicative of the water-cut and/or other properties of the fluid obtained from the formation.

The spectrometer may send optical spectra and/or other data representative of the measured optical characteristics to a processor of the downhole sampling tool 200 and/or associated wellsite surface equipment (not shown). In the context of the present disclosure, the term "processor" refers to any number of processor components. The processor may include a single processor disposed onboard the downhole sampling tool 200. In other implementations, at least a portion of the processor (e.g., in implementations in which multiple processors operate cooperatively) may be located within the wellsite surface equipment. The processor may also or instead be or include one or more processors located within the downhole sampling tool 200 and connected to one or more processors located in drilling and/or other equipment disposed at the wellsite surface. One or more of the processors described above may have one or more aspects in common with at least a portion of the apparatus shown in FIG. 11 and described below.

The pumpout module 235 may comprise one or more electrical, mechanical, hydraulic, and/or other pumps 275 operable to pump fluid (liquid and/or gas) from the one or more probes 210 of the probe module 205 and/or from the one or more ports 225 of the dual-packer module 215. Such fluid transfer may be facilitates by various valves and/or other hydraulic circuitry (not shown) operable in conjunction with the one or more flowlines 255. The one or more pumps 275 may also be operable to pump fluid to the one or more sample chambers 245 of the sample module 240.

The conveyance terminal 250 may provide an interface between a conveyance means 280 and the remainder of the downhole sampling tool 200. For example, the conveyance means 280 may be or include wireline (mono-cable, multi-conductor, and/or others), slickline, e-line, coiled tubing, drill pipe, casing, and/or other conveyance means. The interface provided by the conveyance terminal 250 may be mechanical, electrical (e.g., for power and/or data), hydraulic, pneumatic, and/or otherwise.

One or more other devices, tools, modules, and/or other apparatus 285 may be positioned below the dual-packer module 215. However, the scope of the present disclosure is not limited by the number and/or function of such additional apparatus 285, and such apparatus 285 may not be utilized in each implementation falling within the scope of the present disclosure.

The selected type and/or number of inlets of the downhole sampling tool 200 may depend on a combination of operational goals, formation properties, and/or formation fluid properties, whether such inlets comprise one or more instances of the probe 210, the packer module 215, and/or other fluid inlet means. Each inlet type may be associated with different down-hole pressure and water-cut behaviors during cleanup and/or sampling operations.

Figure 3:
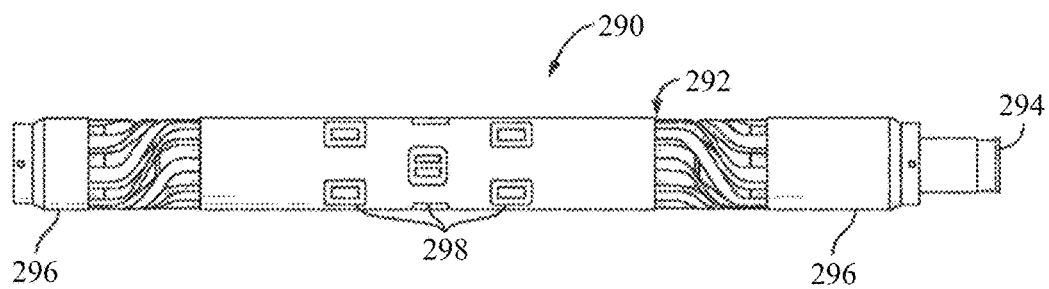
FIG. 3 is a schematic view of at least a portion of an example implementation of apparatus according to one or more aspects of the present disclosure.

Another inlet type within the scope of the present disclosure is a radial probe module, which may be included in the downhole sampling tool 200 shown in FIG. 2, whether instead of or in addition to the probe module 205, the dual packer module 215, or both. An example radial probe module 290 is depicted in FIG. 3, and includes an outer structural layer 292 that is expandable in a wellbore to form a seal with surrounding wellbore wall, an inflatable bladder (obscured from view in FIG. 3) selectively expandable by fluid delivered via an inner mandrel 294, mechanical fittings 296 mounted around the inner mandrel 294 and engaged with axial ends of the outer structural layer 292, and multiple drains 298 through which fluid from the formation is collected when the outer structural layer 292 is expanded against the wellbore wall.

Figure 4:
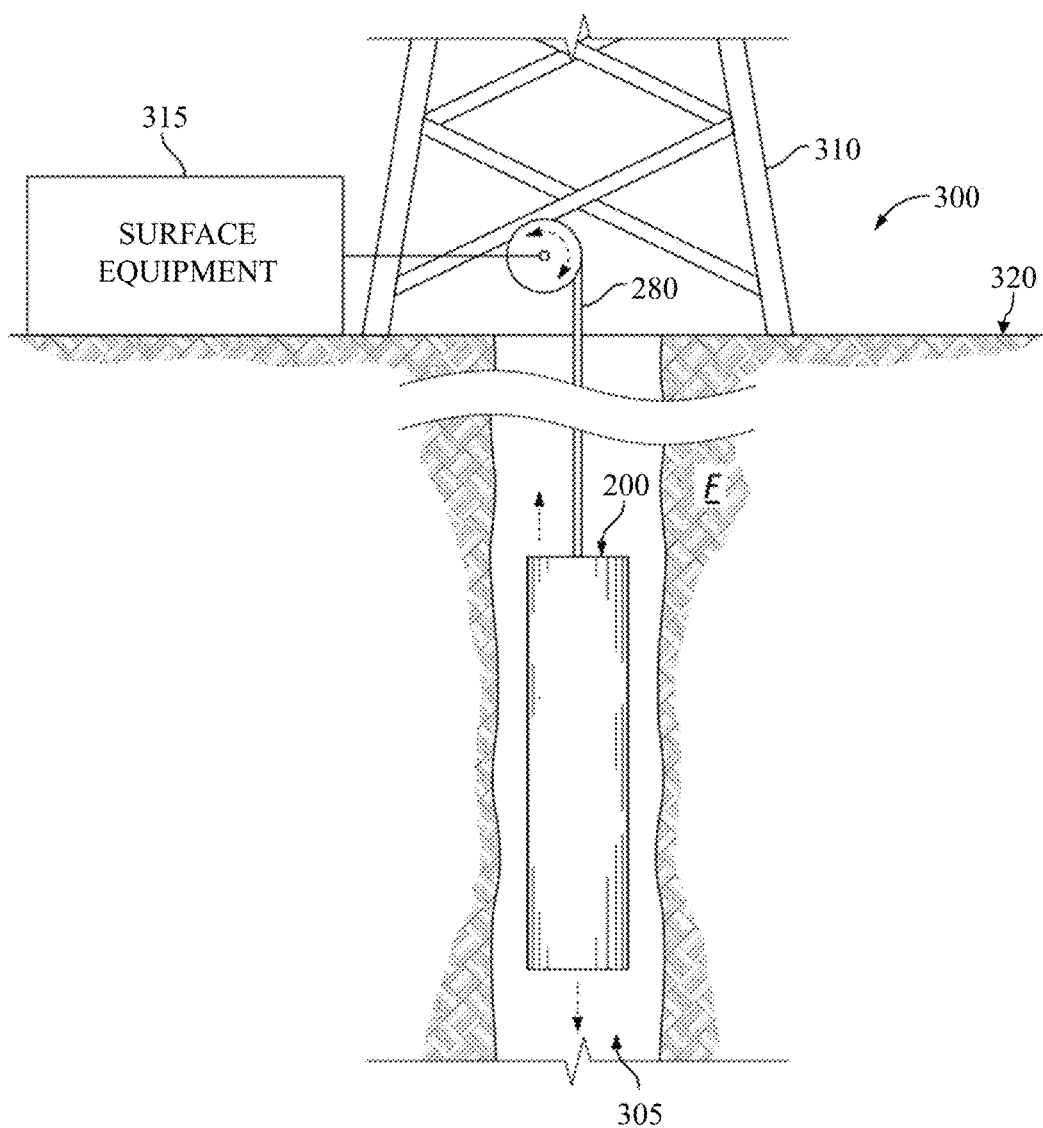
FIG. 4 is a schematic view of at least a portion of an example implementation of apparatus according to one or more aspects of the present disclosure.

FIG. 4 is a schematic view of an example implementation of a wellsite system 300 that may be employed onshore and/or offshore according to one or more aspects of the present disclosure, representing an example environment in which one or more aspects of the downhole sampling tool 200 may be implemented. As depicted in FIG. 4, an implementation of the downhole sampling tool 200 may be suspended from a platform, rig, derrick, and/or other wellsite structure 310 in a wellbore 305 formed in one or more subterranean formations F. The downhole sampling tool 200 may be or comprise one or more tools, modules, and/or apparatus instead of or in addition to those described above and/or shown in FIGS. 2 and 3, one or more of which may be or comprise an acoustic tool, a conveyance tool, a density tool, an electromagnetic (EM) tool, a formation evaluation tool, a magnetic resonance tool, a monitoring tool, a neutron tool, a nuclear tool, a photoelectric factor tool, a porosity tool, a reservoir characterization tool, a resistivity tool, a seismic tool, a surveying tool, and/or a telemetry tool, although other downhole tools are also within the scope of the present disclosure.

The downhole sampling tool 200 may be deployed from the wellsite structure 310 into the wellbore 305 via the conveyance means 280. As the downhole sampling tool 200 operates, outputs of various numbers and/or types from the downhole sampling tool 200 and/or components thereof may be sent via to a logging and control system and/or other surface equipment 315 at surface 320, and/or may be stored in various numbers and/or types of memory for subsequent recall and/or processing after the downhole sampling tool 200 is retrieved to surface 320. The downhole sampling tool 200 and/or one or more components thereof may thus be utilized to perform at least a portion of a method according to one or more aspects of the present disclosure.

The following operation of the downhole sampling tool 200 is described in the context of the wellbore 305 having been formed by a drilling operation utilizing WBM. However, aspects of the description are similarly applicable to implementations in which the wellbore 305 was formed by a drilling operation utilizing OBM.

During operation of the downhole sampling tool 200 shown in one or more of FIGS. 2-4 and/or otherwise within the scope of the present disclosure, a cleanup procedure may commence with the setting an inlet (e.g., one or more probes, packer intervals, etc.) to a sidewall of the wellbore 305, such as to a sandface of the formation F, and performing one or more pressure measurements. Such pressure measurements may be part of what may be referred to as a "pretest" by a person having ordinary skill in the art, and/or may aid in facilitating fluid communication between the formation F and the downhole sampling tool 200. Pretesting may also comprise measuring, estimating, and/or otherwise obtaining the formation pressure and mobility (k/μ; [=permeability/viscosity]), which may be utilized to obtain an indication of permeability expected in the formation F. Mobility may not be converted directly to the permeability due to, for example, depth of investigation, the effects of relative permeabilities, and the damage zone introduced by the mud filtrate invasion. Pretesting may utilize a volume of fluid pumped from the formation F that may be less than about twenty cubic centimeters with a single probe, or up to about three liters with a radial probe or dual-packer module, among other possible amounts and/or examples also within the scope of the present disclosure.

The pump/pump module may then be operated to pump fluid from the formation F into the downhole sampling tool 200 and then into the wellbore 305. During such time, the pump rate may be adjusted to achieve a certain drawdown pressure, and the fluid analyzer of the downhole sampling tool 200 may monitor the pumped fluid. Initially, perhaps about 100% mud filtrate may flow from the formation F, followed by formation fluid with a receding water-cut. The fluid analyzer may provide drawdown pressure, fluid composition, water-cut, GOR, density, viscosity, and/or other parameters as the pumping continues. The cleanup operation may be deemed sufficient when water-cut falls to less than a predetermined level, such as about ten percent, although other levels are also within the scope of the present disclosure.

In implementations in which a dual-packer module is utilized, the dual-packer module may be operable to isolate an interval of the wellbore having an axial length of about one meter, and the inlet port within the isolated interval may be located about 33 centimeters from the top of the lower packer. This results in a sump volume of about seventeen liters residing between the upper and lower packers when utilized in an uncased wellbore having a diameter of about 21.6 centimeters. The fluid that collects in the dual-packer interval will segregate, with oil congregating above water. Thus, a volume of oil accumulates in the dual-packer interval before entering the downhole sampling tool through the inlet port of the dual packer module. A numerical simulation according to one or more aspects of the present disclosure, utilizing a multi-segment well module/model, may account for this segregation in the dual-packer interval.

Homogeneous flow models may not account for slip between the fluid phases, and may instead model the fluid phases as collectively moving at the same velocity. The hydrostatic term depends on the density of the fluid mixture, which may be a flow-weighted average of the phase densities. In reality, fluid phases may have different in situ velocities, depending on the differences between density and/or viscosity of the individual phases, for example. Such differences may be exacerbated in implementations utilizing a dual-packer module.

ECLIPSE 100 is a black oil numerical simulator commercially available from SCHLUMBERGER, among other simulator examples that may be utilized according to one or more aspects of the present disclosure. For example, in ECLIPSE 100, an inflow performance relationship is written in terms of the volumetric production rate of each phase at stock tank conditions, as set forth below in Equation (1).

$$q_{p,j} = T_{wj} M_{p,j}(P_j - P_w - H_{wj}) \quad (1)$$

where:
$q_{p,j}$ is volumetric flow rate of phase p in connection j at stock tank conditions;
$T_{wj}$ is the connection transmissibility factor in connection j;
$M_{p,j}$ is mobility of phase p in connection j;
$P_j$ is nodal pressure in the grid block containing connection j;
$P_w$ is bottom-hole pressure of the well; and $H_{wj}$ is wellbore pressure head between the connection j and the well's bottom hole datum depth.

The present disclosure introduces a drift-flux model to, for example, account for the segregation of fluids in the dual-packer interval, which may have a substantial effect on the native formation fluid breakthrough time. The drift-flux model may also account for the slip between the fluid phases when flowing in the wellbore. The drift-flux model may also model counter-current flow, which may permit the heavy and light phases to move in opposite directions when the overall flow velocity is small or when the well is shut in.

In ECLIPSE 100, a radial or other gridding technique may be utilized for modeling fluid flow from the formation. The flow of fluid between a grid block and the node of an associated segment is given by an inflow performance relationship, as set forth below in Equation (2).

$$q_{p,j} = T_{wj} M_{p,j} (P_j + H_{cj} - P_n - H_{nc}) \quad (2)$$

where:
$H_{cj}$ is hydrostatic pressure head between the center depth of the grid block and the depth of connection j;
$P_n$ is pressure at the associated segment's node n; and
$H_{n\ c}$ is hydrostatic pressure head between the segment node n and the connection depth.

The friction pressure loss in the drift-flux model may be based on the formulation utilized for correlation as set forth below in Equation (3).

$$\delta P_f = \frac{C_f f L w^2}{A^2 D \rho} \quad (3)$$

where:
$\delta P_f$ is friction pressure loss;
$C_f$ is a units conversion constant;
f is a fanning friction factor;
L is length of the segment;
w is mass flow rate of the fluid mixture through the segment;
A is cross-sectional flow area of the segment;
D is diameter of the segment; and
ρ is in-situ density of the fluid mixture.

The acceleration pressure loss across a segment in the drift-flux model is the difference between the velocity head of the mixture flowing across the outlet junction of the segment and the velocity heads of the mixture flowing through each of the inlet junctions, such as the main inlet and the side branches connecting with the segment, as set forth below in Equation (4).

$$\delta P_a = H_{vout} - \Sigma_{inlets} H_{vin} \quad (4)$$

where:
$\delta P_a$ is acceleration pressure loss across a segment;
$H_{vout}$ is velocity head of the mixture flowing across the outlet junction of the segment; and
$H_{vin}$ is velocity head of the mixture flowing through an inlet junction.

The velocity head of the mixture flowing through a junction ($H_v$) may be expressed as set forth below in Equation (5).

$$H_v = \frac{0.5 C_f w^2}{A^2 \rho} \quad (5)$$

For the outlet junction flow, A is the cross-sectional area of the segment. For inlet junction flows, A is the maximum of the cross-sectional areas of the segment and the inlet segment.

The drift-flux model may express the gas-liquid slip as a combination of two mechanisms. The first mechanism results from the non-uniform distribution of gas across the cross-section of a pipe, and the velocity profile across the pipe. The concentration of gas in the gas-liquid mixture tends to be greater nearer the center of the pipe and smaller near the pipe wall. The local flow velocity of the mixture is also greatest at the center of the pipe. Thus, when integrated across the area of the pipe, the average velocity of the gas tends to be greater than that of the liquid. The second mechanism results from the tendency of gas to rise vertically through the liquid due to buoyancy. A formulation that combines the two mechanisms is set forth below in Equations (6) and (7).

$$v_g = C_0 j + v_d \quad (6)$$

$$j = v_{sg} + v_{sl} = \alpha_g v_g + (1 - \alpha_g) v_l \quad (7)$$

where:
$v_g$ is flow velocity of the gas phase, averaged across the pipe area;
$C_0$ is a profile parameter (or distribution coefficient) resulting from the velocity and gas concentration profiles;
j is volumetric flux of the mixture;
$v_d$ is drift velocity of the gas phase;
$v_{sg}$ is gas superficial velocity;
$v_{sl}$ is liquid superficial velocity;
$\alpha_g$ is gas volume fraction, averaged across the pipe area; and
$v_l$ is average liquid flow velocity.

The average liquid flow velocity may then be expressed as set forth below in Equation (8).

$$v_l = \frac{1 - \alpha_g C_0}{1 - \alpha_g} j - \frac{\alpha_g}{1 - \alpha_g} v_d \quad (8)$$

It has been shown that the value of $C_0$ may range between about 1.0 and about 1.5. Some flow correlations assume a value of 1.2 to apply in the bubble and slug flow regimes. Thus, for example, $C_0$ may be set to a constant value of 1.2 at low values of $\alpha_g$ and j. However, other values are also within the scope of the present disclosure.

The expression for the drift velocity may be derived by combining data at the limits of counter-current flow made under a variety of flowing conditions, and then interpolating to avoid discontinuities. Such method may honor observations of gas-liquid relative velocities at low and high gas volume fractions, such as by joining them with a "flooding curve," for example.

The rise velocity of gas through a stationary liquid may be expressed as set forth below in Equation (9).

$$v_g(v_l = 0) = \frac{v_d}{1 - \alpha_g C_0} \quad (9)$$

As it approaches zero, the gas velocity will approach the rise velocity of a single bubble, for which the value of the characteristic velocity location ($v_c$) may be as set forth below in Equation (10).

$$v_c = \left[\frac{\sigma_{gl}g(\rho_l - \rho_g)}{\rho_l^2}\right]^{1/4} \quad (10)$$

where:
$\sigma_{gl}$ is gas-liquid interfacial tension;
g is gravitational acceleration;
$\rho_l$ is liquid phase density; and
$\rho_g$ is gas phase density.

The drift-flux model described above is formulated for two-phase, gas-liquid mixtures. For three-phase mixtures flowing in the wellbore, and for oil-water mixtures, the following model may be applied.

For three-phase mixtures, the above formulation is utilized to model the total slip between the gas phase and the combined liquid phase. The properties of the combined liquid phase (such as density and viscosity, among others) may be calculated as an average of the oil and water properties, weighted according to the volume fraction of each phase. This treatment may neglect the potential tendency of the oil-water mixture to form emulsions, but may nonetheless be utilized to apply two-phase flow correlations to oil-water-gas mixtures in a well. The gas-liquid interfacial tension may then be determined as set forth below in Equation (11).

$$\sigma_{gl} = \frac{\alpha_o \sigma_{go} + \alpha_w \sigma_{wg}}{\alpha_o + \alpha_w} \quad (11)$$

where:
$\alpha_o$ is oil volume fraction;
$\sigma_{go}$ is gas-oil interfacial tension;
$\alpha_w$ is water volume fraction; and
$\sigma_{wg}$ is water-gas interfacial tension.

In Equation (11), $\sigma_{go}$, and $\sigma_{wg}$ may be supplied or determined from built-in correlations. The velocity of the combined liquid phase may be obtained, and then the drift-flux oil-water slip model maybe utilized to resolve the velocities of the oil and water phases. The slip between oil and water in the liquid phase may be as expressed below in Equation (12).

$$v_o = C'_0 v_l + v'_d \quad (12)$$

where:
$v_o$ is the slip between oil and water in the liquid phase;
$C'_0$ profile parameter between oil and water phases;
$v'_d$ is oil-liquid drift velocity.

The holdup fraction of oil in the liquid phase ($\alpha_{ol}$) may be as set forth below in Equation (13).

$$\alpha_{ol} = \alpha_o/(\alpha_o + \alpha_w) \quad (13)$$

From the above, the oil-liquid drift velocity may be determined as set forth below in Equations (14) and (15).

$$v'_d = 1.53 v'_c (1-\alpha_{ol})^2 \quad (14)$$

where:

$$v'_c = \left[\frac{\sigma_{ow}g(\rho_w - \rho_o)}{\rho_w^2}\right]^{1/4} \quad (15)$$

and:
$\sigma_{ow}$ is oil-water interfacial tension;
$\rho_w$ is water density; and
$\rho_o$ is oil density.

Thus, the slip between oil and water in the liquid phase may be modeled/expressed as set forth above in Equations (14) and (15).

Figure 5:
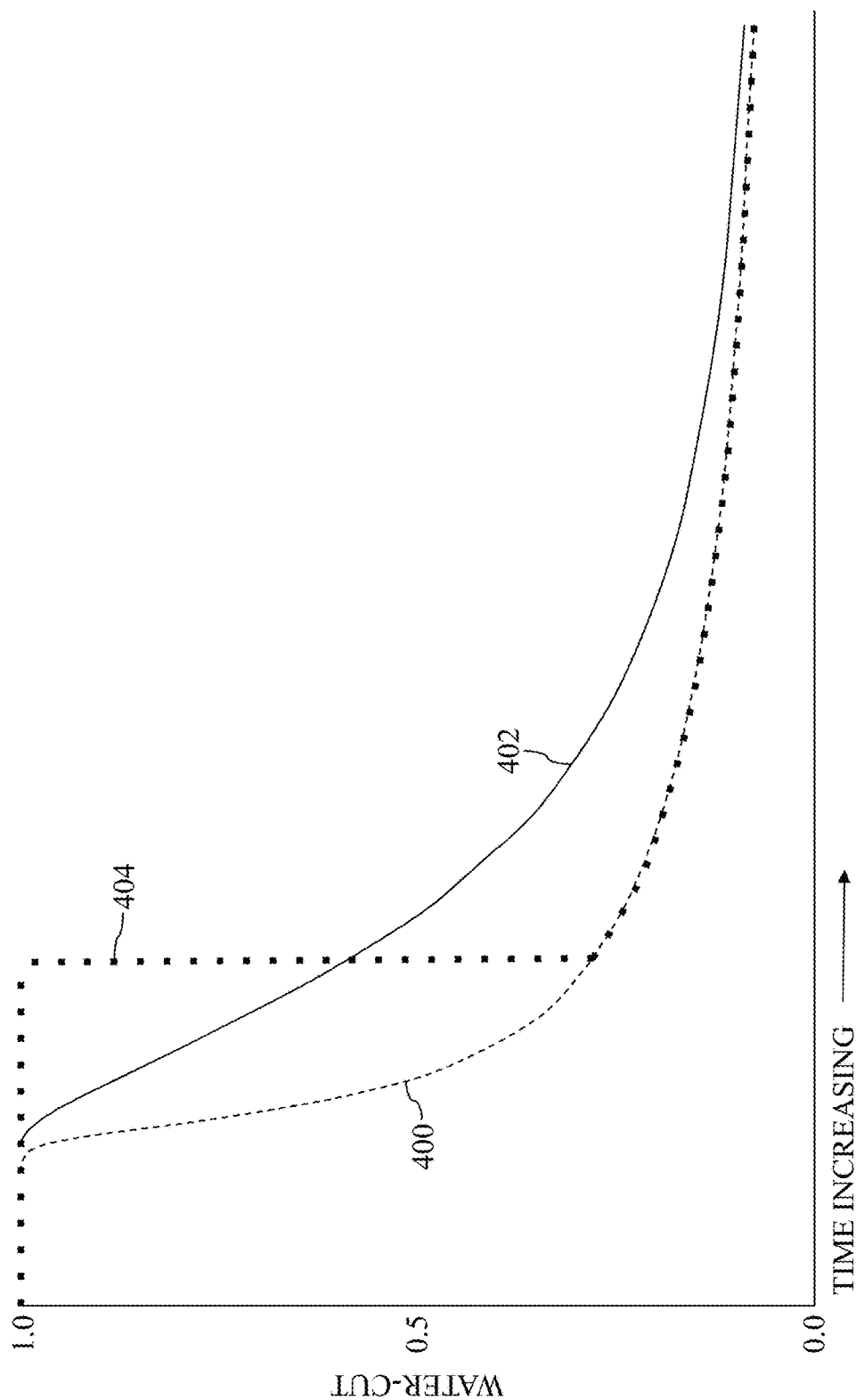
FIG. 5 is a graph depicting one or more aspects of the present disclosure.

FIG. 5 is a graph depicting example water-cut progression during a cleanup operation according to one or more aspects of the present disclosure. The graph includes a first curve 400 depicting the water-cut progression based on a homogeneous flow model for a downhole sampling tool utilizing a dual-packer module, which has no interval volume, to obtain fluid from the formation at the sandface, and a second curve 402 depicting the water-cut progression based on a homogeneous flow model for a downhole sampling tool utilizing a dual-packer module, which has an interval volume. As shown in FIG. 5, the homogeneous flow model for the dual-packer module (402) indicates a slower, less accurate water-cut progression, which ignores the fluid segregation in the interval and, due to the interval volume, cleanup is delayed in comparison to the curve 400. The graph also includes a third curve 404 depicting the water-cut progression based on a drift-flux flow model, which accounts for slip velocities, hydrostatic, friction, and acceleration terms, when utilizing the dual-packer module with an interval volume, indicating a more accurate water-cut progression.

The graph demonstrates the cleanup behavior in the field operation as being similar to the drift-flux flow model, including the late arrival of hydrocarbon. Previous models relying on homogenous flow having either a dual-packer interval volume or no interval volume may not accurately predict the correct hydrocarbon breakthrough time. The reduction of mud filtrate is related to the increase of hydrocarbon during cleanup. When hydrocarbons arrive in the dual-packer interval, they segregate and accumulate in the upper part of the dual-packer interval. This delays the hydrocarbons arriving at the inlet port located in the lower part of the dual-packer interval, because the lower part of the dual-packer interval is still filled with the WBM filtrate. Hydrocarbons further accumulate over time and move downward in the dual-packer interval. This segregation is accounted for by the drift-flux flow model, which provides the correct volume of the fluids and the delay of their detection due to the sandface-to-fluid analyzer distance.

History matching of the above-described numerical model to actual downhole data may be achieved by various optimization techniques within the scope of the present disclosure. Gradient-based, stochastic, and/or other optimization techniques may be utilized, for example, including to check accuracy and speed. The optimization may run several sensitivity cases of the numerical model with a given range of parameters to achieve history matching. Mismatch of the simulated theoretical data to the actual data may be quantified by an objective function, and the optimization may operate by attempting to minimize the value of the objective function.

In gradient-based optimization, the gradient of the objective function is utilized to calculate or otherwise determine successive search directions that may eventually converge to a (local) minimum. Using the gradient information, the optimization may determine the changes utilized in the history matching parameters to further reduce the objective function. The process may be repeated until an acceptable history match is achieved or further progress is unattainable. The "best" or most acceptable history match may provide the actual relative permeabilities and capillary pressures.

Stochastic optimization methods utilize a random sampling to minimize the objective function and obtain parameter values while attempting history matching (minimizing the objective function). The parameters may be model inputs and/or functions that calculate or otherwise determine the model inputs. The parameters may include damage skin, depth of mud filtrate invasion, curvature exponents, endpoint saturations of relative permeabilities, and capillary pressure end points. An example parameter sampling strategy is the "Latin Hyper Cube," which screens the entire parameter ranges in equally large compartments. Stochastic methods may not guarantee global minimum, but may be practical for utilization during history matching processes because they do not entirely explore the search space.

The optimization may also or instead utilize Monte Carlo optimization methods, which are a wide-ranging category of numerical optimizations that depend on repeated random sampling to obtain numerical simulation results. Numerical simulations may be run periodically to obtain the distribution of an unknown probabilistic parameter.

The history matching is an inverse process where relative permeabilities and capillary pressures are optimized with one or more parameters. Automation may be established by linking commercial software, such as ECLIPSE 100, SIMOPT gradient-based optimization software, and MEPO stochastic-based optimization software. The "best" history match may provide actual relative permeability and capillary pressure curves with statistically defined uncertainties.

Figure 6:
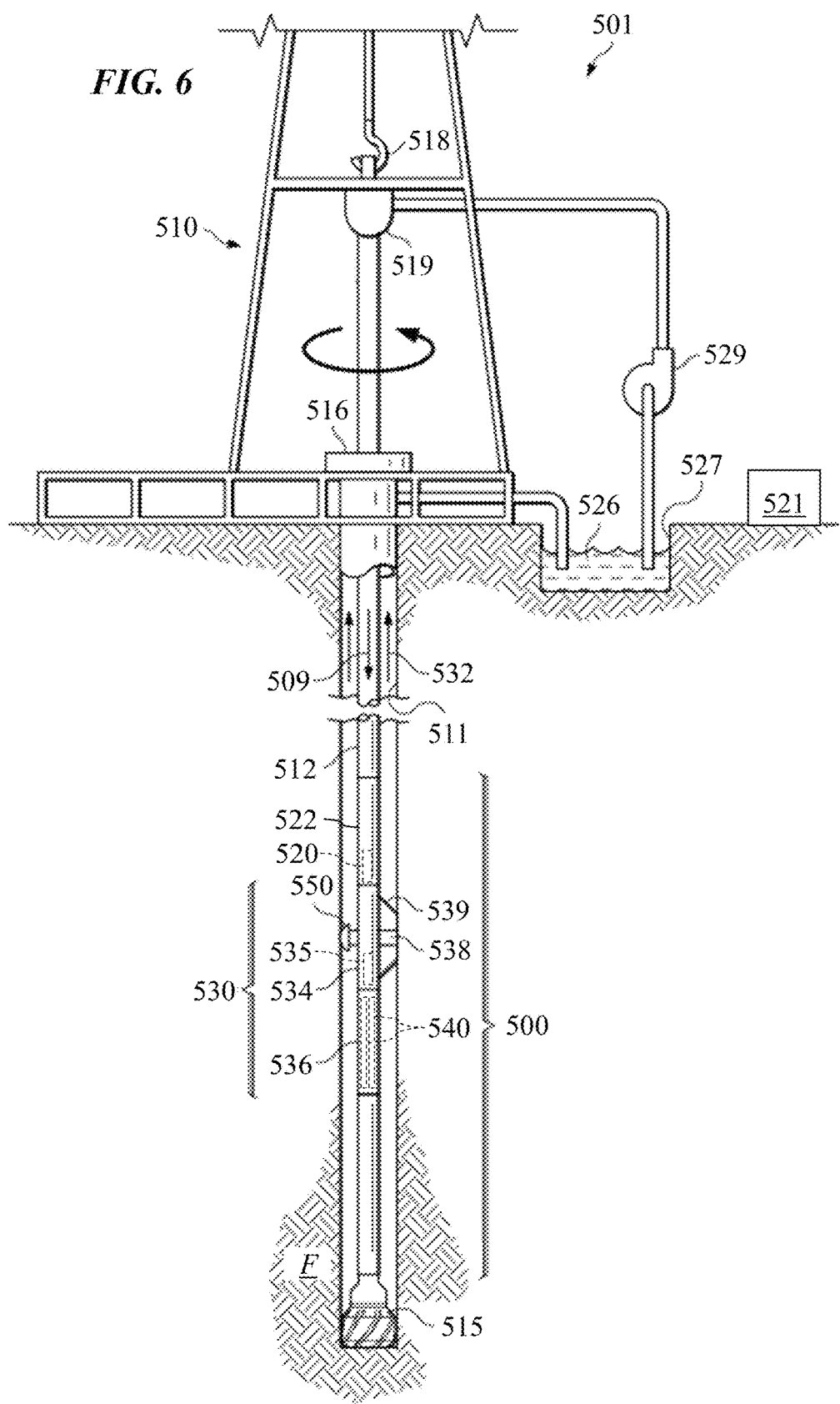
FIG. 6 is a schematic view of at least a portion of an example implementation of apparatus according to one or more aspects of the present disclosure.

While at least portions of the above description are presented in the context of a downhole sampling tool conveyed via wireline, one or more such aspects may also be applicable or readily adaptable to while-drilling and other drillstring-conveyed apparatus. For example, FIG. 6 is a schematic view of at least a portion of apparatus that may be utilized, or adapted for utilization with, one or more aspects of the present disclosure. Depicted components include a wellsite 501, a rig 510, and a downhole sampling tool 500 suspended from the rig 510 in a wellbore 511 via a drillstring 512. The downhole sampling tool 500, or a bottom hole assembly ("BHA") comprising the downhole sampling tool 500, may have one or more modules, tools, features, and/or other aspects similar in function to corresponding aspects of the downhole sampling tool 200 shown in FIGS. 2-4 and described above.

The downhole sampling tool 500 comprises or is coupled to a drill bit 515 that is used to advance the downhole sampling tool 500 into the formation F and form the wellbore 511. The drillstring 512 may be rotated by a rotary table 516 that engages a kelly at the upper end of the drillstring. The drillstring 512 is suspended from a hook 518 attached to a traveling block (not shown) and a rotary swivel 519 that permits rotation of the drillstring 512 relative to the hook 518.

The rig 510 is depicted as a land-based platform and derrick assembly utilized to form the wellbore 511 by rotary drilling in a manner that is well known. A person having ordinary skill in the art will appreciate, however, that one or more aspects of the present disclosure may also find application in other downhole applications, such as rotary drilling, and is not limited to land-based rigs.

Drilling fluid (WBM or OBM) 526 is stored in a pit 527 formed at the well site. A pump 529 delivers the drilling fluid 526 to the interior of the drillstring 512 via a port in the swivel 519, inducing the drilling fluid 526 to flow downward through the drillstring 512, as indicated in FIG. 6 by directional arrow 509. The drilling fluid 526 exits the drillstring 512 via ports in the drill bit 515, and then circulates upward through the annulus defined between the outside of the drillstring 512 and the wall of the wellbore 511, as indicated by direction arrows 532. In this manner, the drilling fluid 526 lubricates the drill bit 515 and carries formation cuttings up to the surface as it is returned to the pit 527 for recirculation.

The downhole sampling tool 500 comprises various components with various capabilities, such as measuring, processing, and storing information. A telemetry device 522 is also provided for communicating with a surface unit 521.

The downhole sampling tool 500 also comprises a sampling while drilling ("SWD") system 530 comprising a fluid communication module 534 and a sample module 536, which may be individually or collectively housed in one or more drill collars for performing various formation evaluation and/or sampling functions. The fluid communication module 534 may be positioned adjacent the sample module 536, and may comprise one or more pumps 535, gauges, sensor, monitors and/or other devices that may also be utilized for downhole sampling and/or testing. The downhole sampling tool 500 shown in FIG. 6 is depicted as having a modular construction with specific components in certain modules. However, the downhole sampling tool 500 may be unitary, or select portions thereof may be modular. The modules and/or the components therein may be positioned in a variety of configurations throughout the downhole sampling tool 500.

The fluid communication module 534 comprises a fluid communication device 538 that may be positioned in a stabilizer blade or rib 539. The fluid communication device 538 may be or comprise one or more probes, inlets, and/or other means for receiving sampled fluid from the formation F and/or the wellbore 511. The fluid communication device 538 also comprises a flowline (not shown) extending into the downhole sampling tool 500 for passing fluids therethrough. The fluid communication device 538 may be movable between extended and refracted positions for selectively engaging a wall of the wellbore 511 and acquiring one or more fluid samples from the formation F. The fluid communication module 534 may also comprise a back-up piston 550 operable to assist in positioning the fluid communication device 538 against the wall of the wellbore 511.

The sample module 536 comprises one or more sample chambers 540. The sample chambers 540 may be detachable from the sample module 536 at surface, and may be certified for subsequent highway and/or other transportation.

The downhole sampling tool 500 may also comprise a downhole controller and/or control system 520 operable to communicate with surface equipment 521. The downhole controller and/or control system 520 may be configured to control the telemetry device 522, the SWD system 530, and/or other modules, components, and/or features for the extraction of fluid from the formation F.

Figure 7:
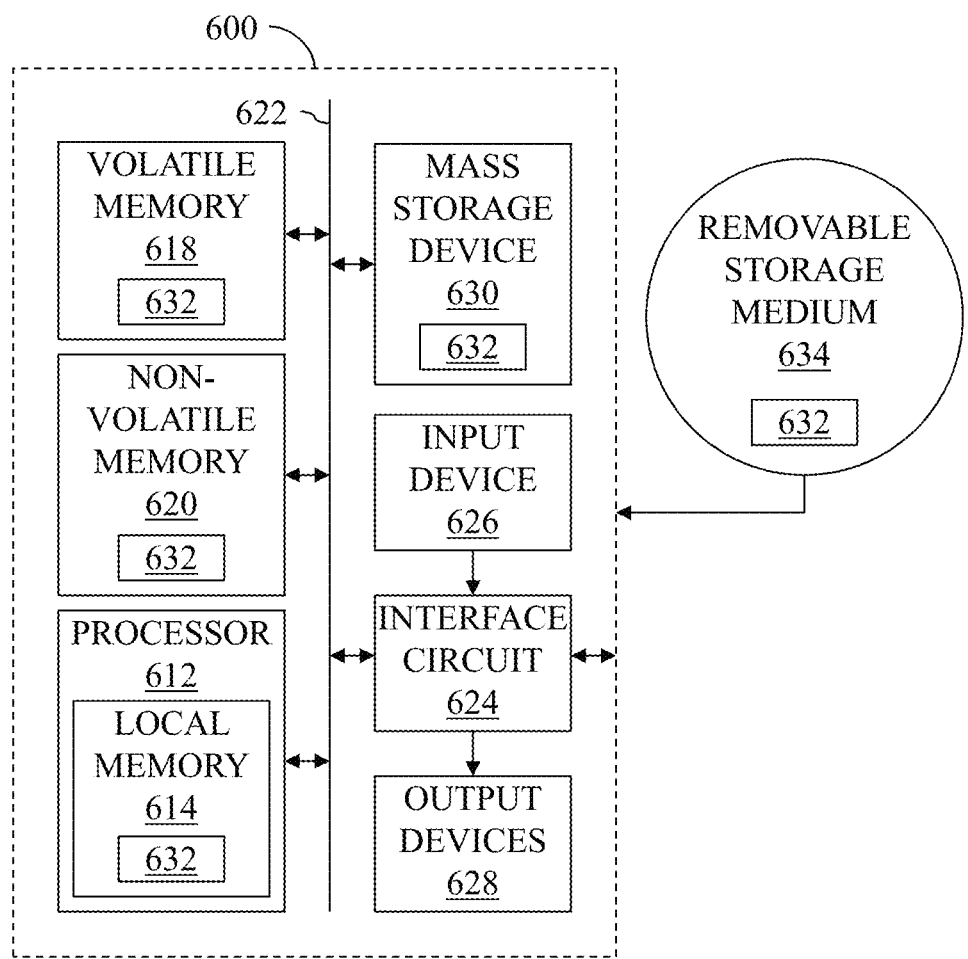
FIG. 7 is a schematic view of at least a portion of an example implementation of apparatus according to one or more aspects of the present disclosure.

FIG. 7 is a schematic view of at least a portion of apparatus according to one or more aspects of the present disclosure. The apparatus is or comprises a processing system 600 that may execute example machine-readable instructions to implement at least a portion of one or more of the methods and/or processes described herein, and/or to implement at least a portion of one or more of the example downhole modules, tools, tool strings, components, processors, controllers, and/or other apparatus described herein. For example, the apparatus may perform at least a portion of the method (100) shown in FIG. 1, such as to obtain (110) the model predicting water-cut and pressure, with respect to cleanup time, based on estimated relative permeabilities and capillary pressures, and/or to update (130) the model utilizing actual sampling operation data to obtain actual relative permeabilities and capillary pressures. In such implementations, the apparatus may be located at the wellsite, such as when the apparatus is implemented within the surface equipment 315 shown in FIG. 4 and/or the surface unit/equipment 521 shown in FIG. 6, or the apparatus may be located remote from the wellsite.

The processing system 600 may be or comprise, for example, one or more processors, controllers, special-purpose computing devices, servers, personal computers, personal digital assistant ("PDA") devices, smartphones, internet appliances, and/or other types of computing devices. Moreover, while it is possible that the entirety of the processing system 600 shown in FIG. 7 is implemented within downhole apparatus shown in one or more of FIGS. 2-4 and 6, and/or other downhole apparatus within the scope of the present disclosure, it is also contemplated that one or more processors, components, and/or functions of the processing system 600 may be implemented in wellsite surface equipment, perhaps including at least a portion of the surface equipment 315 depicted in FIG. 4, the surface unit/equipment 521 depicted in FIG. 6, and/or other surface equipment, as well as equipment located remote from the wellsite.

The processing system 600 may comprise a processor 612 such as, for example, a general-purpose programmable processor. The processor 612 may comprise a local memory 614, and may execute coded instructions 632 present in the local memory 614 and/or another memory device. The processor 612 may execute, among other things, machine-readable instructions or programs to implement the methods and/or processes described herein. The programs stored in the local memory 614 may include program instructions or computer program code that, when executed by an associated processor, enable downhole, surface, and/or remote equipment to perform tasks as described herein. The processor 612 may be, comprise, or be implemented by one or a plurality of processors of various types suitable to the local application environment, and may include one or more general-purpose computers, special purpose computers, microprocessors, digital signal processors ("DSPs"), field-programmable gate arrays ("FPGAs"), application-specific integrated circuits ("ASICs"), and/or processors based on a multi-core processor architecture, as non-limiting examples. Of course, other processors from other families are also appropriate.

The processor 612 may be in communication with a main memory, such as may include a volatile memory 618 and a non-volatile memory 620, perhaps via a bus 622 and/or other communication means. The volatile memory 618 may be, comprise, or be implemented by random access memory (RAM), static random access memory (SRAM), synchronous dynamic random access memory (SDRAM), dynamic random access memory (DRAM), RAMBUS dynamic random access memory (RDRAM) and/or other types of random access memory devices. The non-volatile memory 620 may be, comprise, or be implemented by read only memory, flash memory and/or other types of memory devices. One or more memory controllers (not shown) may control access to the volatile memory 618 and/or the non-volatile memory 620.

The processing system 600 may also comprise an interface circuit 624. The interface circuit 624 may be, comprise, or be implemented by various types of standard interfaces, such as an Ethernet interface, a universal serial bus (USB), a third generation input/output (3GIO) interface, a wireless interface, and/or a cellular interface, among others. The interface circuit 624 may also comprise a graphics driver card. The interface circuit 624 may also comprise a communication device, such as a modem or network interface card, to facilitate exchange of data with external computing devices via a network (e.g., via Ethernet connection, digital subscriber line ("DSL"), telephone line, coaxial cable, cellular telephone system, satellite, etc.).

One or more input devices 626 may be connected to the interface circuit 624. The input device(s) 626 may permit a user to enter data and commands into the processor 612. The input device(s) 626 may be, comprise, or be implemented by, for example, a keyboard, a mouse, a touchscreen, a track-pad, a trackball, an isopoint, and/or a voice recognition system, among others.

One or more output devices 628 may also be connected to the interface circuit 624. The output devices 628 may be, comprise, or be implemented by, for example, display devices (e.g., a liquid crystal display or cathode ray tube display (CRT), among others), printers, and/or speakers, among others.

The processing system 600 may also comprise one or more mass storage devices 630 for storing machine-readable instructions and data. Examples of such mass storage devices 630 include floppy disk drives, hard drive disks, compact disk (CD) drives, flash drives, and digital versatile disk (DVD) drives, among others. The coded instructions 532 may be stored in the mass storage device 630, the volatile memory 618, the non-volatile memory 620, the local memory 614, and/or on a removable storage medium 634, such as a CD, DVD, or flash drive. Thus, the modules and/or other components of the processing system 600 may be implemented in accordance with hardware (embodied in one or more chips including an integrated circuit such as an application specific integrated circuit), or may be implemented as software or firmware for execution by a processor. In particular, in the case of firmware or software, the embodiment can be provided as a computer program product including a computer readable medium or storage structure embodying computer program code (i.e., software or firmware) thereon for execution by the processor.

In view of the entirety of the present disclosure, including the claims and the figures, a person having ordinary skill in the art should readily recognize that the present disclosure introduces a method comprising: operating an apparatus to obtain a model predicting data associated with a theoretical sampling operation to be performed by a downhole sampling tool, wherein the predicted data comprises predicted water-cut and drawdown pressure data relative to time elapsed during the theoretical sampling operation, and wherein the model predicts the time-based water-cut and drawdown pressure data based on estimated relative permeability and capillary pressure related to different constituents of fluid theoretically obtained from a subterranean formation by the downhole sampling tool during the theoretical sampling operation; performing an actual sampling operation with the downhole sampling tool to actually obtain fluid from the subterranean formation and actual data associated with the actually obtained fluid, wherein the actual data comprises actual water-cut and drawdown pressure data relative to time elapsed during the actual sampling operation; and operating the apparatus to update the model utilizing the actual data water-cut and drawdown pressure data, thus obtaining actual relative permeability and capillary pressure related to different constituents of the actual fluid obtained during the actual sampling operation.

Updating the model may comprise iteratively adjusting the estimated relative permeability and capillary pressure until the predicted water-cut and drawdown pressure data substantially matches the actual water-cut and drawdown pressure data. Updating the model may utilize gradient optimization, deterministic optimization, or stochastic optimization, or a combination thereof.

The actual sampling operation may be performed with the downhole sampling tool disposed in a wellbore extending into the subterranean formation, and performing the actual sampling operation may comprise: isolating an interval of the wellbore by extending two packers of the downhole sampling tool into substantially sealing contact with a perimeter of the wellbore; and reducing pressure within the isolated wellbore interval to draw fluid from the subterranean formation into the isolated wellbore interval. In such implementations, the model may be a drift-flux model. Inputs for the drift-flux model may include geometric data related to a dimension or volume of the isolated wellbore interval. The drift-flux model may account for a time delay associated with accumulation of the actually obtained fluid in the isolated wellbore interval before the actually obtained fluid is drawn into the downhole sampling tool.

The actual sampling operation may be performed with the downhole sampling tool disposed in a wellbore extending into the subterranean formation, and performing the actual sampling operation may comprise: establishing substantially sealing contact between an inlet of a probe of the downhole sampling tool and a location on a perimeter of the wellbore; and reducing pressure within the probe inlet to draw fluid from the subterranean formation into the downhole sampling tool. In such implementations, the model may be a homogenous model. Inputs for the homogenous model may include geometric data related to a dimension or volume of the probe inlet.

The fluid theoretically obtained during the theoretical sampling operation and the fluid actually obtained during the actual sampling operation may comprise two immiscible fluids.

The two immiscible fluids may comprise: a first fluid comprising water; and a second fluid comprising hydrocarbons. In such implementations: the wellbore may have been formed in the subterranean formation by a drilling operation utilizing water-based drilling fluid; during early stages of the theoretical and actual sampling operations, the theoretically and actually obtained fluids may comprise substantially more of the first fluid than the second fluid; and during late stages of the theoretical and actual sampling operations, the theoretically and actually obtained fluids may comprise substantially more of the second fluid than the first fluid.

The two immiscible fluids may comprise: a first fluid comprising oil; and a second fluid comprising water. In such implementation: the wellbore may have been formed in the subterranean formation by a drilling operation utilizing oil-based drilling fluid; during early stages of the theoretical and actual sampling operations, the theoretically and actually obtained fluids may comprise substantially more of the first fluid than the second fluid; and during late stages of the theoretical and actual sampling operations, the theoretically and actually obtained fluids may comprise substantially more of the second fluid than the first fluid. The second fluid may further comprise gas.

The present disclosure also introduces a system comprising: a downhole sampling tool operable within a wellbore extending from a wellsite surface into a subterranean formation, wherein the downhole sampling tool is operable to perform an actual sampling operation to actually obtain fluid from the subterranean formation and actual data associated with the actually obtained fluid, wherein the actual data comprises actual water-cut and drawdown pressure data relative to time elapsed during the actual sampling operation; and an apparatus operable to update a model utilizing the actual data water-cut and drawdown pressure data, wherein: the model predicts data associated with a theoretical sampling operation to be performed by the downhole sampling tool; the predicted data comprises predicted water-cut and drawdown pressure data, relative to time elapsed during the theoretical sampling operation, based on estimated relative permeability and capillary pressure related to different constituents of fluid theoretically obtained from the subterranean formation by the downhole sampling tool during the theoretical sampling operation; and updating the model by iteratively adjusting the estimated relative permeability and capillary pressure until the predicted water-cut and drawdown pressure data substantially matches the actual water-cut and drawdown pressure data, thus obtaining actual relative permeability and capillary pressure related to different constituents of the actual fluid obtained during the actual sampling operation.

The downhole sampling tool may comprise a dual-packer module utilized to perform the actual sampling operation. In such implementations, the model may be a drift-flux model. Inputs for the drift-flux model may include geometric data related to a dimension or volume of a wellbore interval isolated by the dual-packer module during the actual sampling operation. The drift-flux model may account for a time delay associated with accumulation of the actually obtained fluid in the isolated wellbore interval before the actually obtained fluid is drawn into the downhole sampling tool.

The downhole sampling tool may comprise a probe utilized to perform the actual sampling operation. In such implementations, the model may be a homogeneous model. Inputs for the homogeneous model may include geometric data related to a dimension or volume of an inlet of the probe.

The present disclosure also introduces a method comprising: operating an apparatus to obtain a model predicting data associated with a theoretical sampling operation to be performed by a downhole sampling tool, wherein the predicted data comprises predicted water-cut and drawdown pressure data relative to time elapsed during the theoretical sampling operation, and wherein the model predicts the time-based water-cut and drawdown pressure data based on estimated relative permeability and capillary pressure related to different constituents of fluid theoretically obtained from a subterranean formation by the downhole sampling tool during the theoretical sampling operation; performing an actual sampling operation with the downhole sampling tool to actually obtain fluid from the subterranean formation, wherein the model is a drift-flux model if the actual sampling operation utilizes a dual-packer module of the downhole sampling tool to actually obtain fluid from the subterranean formation, wherein the model is a homogenous model if the actual sampling operation utilizes a probe of the downhole sampling tool to actually obtain fluid from the subterranean formation, and wherein either the dual-packer module or the probe is utilized to actually obtain fluid from the subterranean formation; obtaining actual data associated with the actually obtained fluid during the actual sampling operation, wherein the actual data comprises actual water-cut and drawdown pressure data relative to time elapsed during the actual sampling operation; and operating the apparatus to update the model by iteratively adjusting the estimated relative permeability and capillary pressure until the predicted water-cut and drawdown pressure data substantially matches the actual water-cut and drawdown pressure data, thus obtaining actual relative permeability and capillary pressure related to different constituents of the actual fluid obtained during the actual sampling operation.

Updating the model may utilize gradient optimization, deterministic optimization, stochastic optimization, or a combination thereof.

Inputs for the model may include geometric data related to a dimension or volume related to the dual-packer module or the probe.

If the actual sampling operation utilizes the dual-packer module to actually obtain fluid from the subterranean formation, the model may account for a time delay associated with accumulation of the actually obtained fluid in a wellbore interval isolated by the dual-packer module before the actually obtained fluid is drawn into the downhole sampling tool.

The fluid theoretically obtained during the theoretical sampling operation and the fluid actually obtained during the actual sampling operation may comprise two immiscible fluids.

The foregoing outlines features of several embodiments so that a person having ordinary skill in the art may better understand the aspects of the present disclosure. A person having ordinary skill in the art should appreciate that they may readily use the present disclosure as a basis for designing or modifying other processes and structures for carrying out the same purposes and/or achieving the same advantages of the embodiments introduced herein. A person having ordinary skill in the art should also realize that such equivalent constructions do not depart from the scope of the present disclosure, and that they may make various changes, substitutions and alterations herein without departing from the spirit and scope of the present disclosure.

The Abstract at the end of this disclosure is provided to comply with 37 C.F.R. § 1.72(b) to permit the reader to quickly ascertain the nature of the technical disclosure. It is submitted with the understanding that it will not be used to interpret or limit the scope or meaning of the claims.

What is claimed is:

1. A method, comprising:
    operating an apparatus to obtain a model predicting data associated with a theoretical sampling operation to be performed by a downhole sampling tool, wherein the predicted data comprises predicted water-cut and drawdown pressure data relative to time elapsed during the theoretical sampling operation, and wherein the model predicts the time-based water-cut and drawdown pressure data based on estimated relative permeability and capillary pressure related to different constituents of fluid theoretically obtained from a subterranean formation by the downhole sampling tool during the theoretical sampling operation;
    performing an actual sampling operation with the downhole sampling tool to actually obtain fluid from the subterranean formation and actual data associated with the actually obtained fluid, wherein the actual data comprises actual water-cut and drawdown pressure data relative to time elapsed during the actual sampling operation; and
    operating the apparatus to update the model utilizing the actual data water-cut and drawdown pressure data, thus obtaining actual relative permeability and capillary pressure related to different constituents of the actual fluid obtained during the actual sampling operation.

2. The method of claim 1 wherein updating the model comprises iteratively adjusting the estimated relative permeability and capillary pressure until the predicted water-cut and drawdown pressure data matches the actual water-cut and drawdown pressure data.

3. The method of claim 2 wherein updating the model utilizes gradient optimization, deterministic optimization, stochastic optimization, or a combination thereof.

4. The method of claim 1 wherein the actual sampling operation is performed with the downhole sampling tool disposed in a wellbore extending into the subterranean formation, and wherein performing the actual sampling operation comprises:
    isolating an interval of the wellbore by extending two packers of the downhole sampling tool into sealing contact with a perimeter of the wellbore; and
    reducing pressure within the isolated wellbore interval to draw fluid from the subterranean formation into the isolated wellbore interval.

5. The method of claim 4 wherein the model is a drift-flux model.

6. The method of claim 4 wherein inputs for the model include geometric data related to a dimension or volume of the isolated wellbore interval.

7. The method of claim 4 wherein the model accounts for a time delay associated with accumulation of the actually obtained fluid in the isolated wellbore interval before the actually obtained fluid is drawn into the downhole sampling tool.

8. The method of claim 1 wherein the actual sampling operation is performed with the downhole sampling tool disposed in a wellbore extending into the subterranean formation, and wherein performing the actual sampling operation comprises:
    establishing sealing contact between an inlet of a probe of the downhole sampling tool and a location on a perimeter of the wellbore; and
    reducing pressure within the probe inlet to draw fluid from the subterranean formation into the downhole sampling tool.

9. The method of claim 8 wherein the model is a homogenous model.

10. The method of claim 8 wherein inputs for the model include geometric data related to a dimension or volume of the probe inlet.

11. The method of claim 1 wherein:
    the fluid theoretically obtained during the theoretical sampling operation and the fluid actually obtained during the actual sampling operation comprise two immiscible fluids, including a first fluid comprising water and a second fluid comprising hydrocarbons;
    the wellbore was formed in the subterranean formation by a drilling operation utilizing water-based drilling fluid;
    during early stages of the theoretical and actual sampling operations, the theoretically and actually obtained fluids comprise more of the first fluid than the second fluid; and
    during late stages of the theoretical and actual sampling operations, the theoretically and actually obtained fluids comprise more of the second fluid than the first fluid.

12. The method of claim 1 wherein:
    the fluid theoretically obtained during the theoretical sampling operation and the fluid actually obtained during the actual sampling operation comprise two immiscible fluids, including a first fluid comprising oil and a second fluid comprising water;
    the wellbore was formed in the subterranean formation by a drilling operation utilizing oil-based drilling fluid;

during early stages of the theoretical and actual sampling operations, the theoretically and actually obtained fluids comprise more of the first fluid than the second fluid; and during late stages of the theoretical and actual sampling operations, the theoretically and actually obtained fluids comprise more of the second fluid than the first fluid.

13. A system, comprising:

a downhole sampling tool operable within a wellbore extending from a wellsite surface into a subterranean formation, wherein the downhole sampling tool is operable to perform an actual sampling operation to actually obtain fluid from the subterranean formation and actual data associated with the actually obtained fluid, wherein the actual data comprises actual water-cut and drawdown pressure data relative to time elapsed during the actual sampling operation; and an apparatus operable to update a model utilizing the actual data water-cut and drawdown pressure data, wherein:

the model predicts data associated with a theoretical sampling operation to be performed by the downhole sampling tool;

the predicted data comprises predicted water-cut and drawdown pressure data, relative to time elapsed during the theoretical sampling operation, based on estimated relative permeability and capillary pressure related to different constituents of fluid theoretically obtained from the subterranean formation by the downhole sampling tool during the theoretical sampling operation; and updating the model by iteratively adjusting the estimated relative permeability and capillary pressure until the predicted water-cut and drawdown pressure data matches the actual water-cut and drawdown pressure data, thus obtaining actual relative permeability and capillary pressure related to different constituents of the actual fluid obtained during the actual sampling operation.

14. The system of claim 13 wherein:

the downhole sampling tool comprises a dual-packer module utilized to perform the actual sampling operation;

the model is a drift-flux model;

inputs for the drift-flux model include geometric data related to a dimension or volume of a wellbore interval isolated by the dual-packer module during the actual sampling operation; and the drift-flux model accounts for a time delay associated with accumulation of the actually obtained fluid in the isolated wellbore interval before the actually obtained fluid is drawn into the downhole sampling tool.

15. The system of claim 13 wherein:

the downhole sampling tool comprises a probe utilized to perform the actual sampling operation;

the model is a homogeneous model; and inputs for the homogeneous model include geometric data related to a dimension or volume of an inlet of the probe.

16. A method, comprising:

operating an apparatus to obtain a model predicting data associated with a theoretical sampling operation to be performed by a downhole sampling tool, wherein the predicted data comprises predicted water-cut and drawdown pressure data relative to time elapsed during the theoretical sampling operation, and wherein the model predicts the time-based water-cut and drawdown pressure data based on estimated relative permeability and capillary pressure related to different constituents of fluid theoretically obtained from a subterranean formation by the downhole sampling tool during the theoretical sampling operation;

performing an actual sampling operation with the downhole sampling tool to actually obtain fluid from the subterranean formation, wherein the model is a drift-flux model if the actual sampling operation utilizes a dual-packer module of the downhole sampling tool to actually obtain fluid from the subterranean formation, wherein the model is a homogenous model if the actual sampling operation utilizes a probe of the downhole sampling tool to actually obtain fluid from the subterranean formation, and wherein either the dual-packer module or the probe is utilized to actually obtain fluid from the subterranean formation;

obtaining actual data associated with the actually obtained fluid during the actual sampling operation, wherein the actual data comprises actual water-cut and drawdown pressure data relative to time elapsed during the actual sampling operation; and operating the apparatus to update the model by iteratively adjusting the estimated relative permeability and capillary pressure until the predicted water-cut and drawdown pressure data matches the actual water-cut and drawdown pressure data, thus obtaining actual relative permeability and capillary pressure related to different constituents of the actual fluid obtained during the actual sampling operation.

17. The method of claim 16 wherein updating the model utilizes gradient optimization, deterministic optimization, stochastic optimization, or a combination thereof.

18. The method of claim 16 wherein inputs for the model include geometric data related to a dimension or volume related to the dual-packer module or the probe.

19. The method of claim 16 wherein, if the actual sampling operation utilizes the dual-packer module to actually obtain fluid from the subterranean formation, the model accounts for a time delay associated with accumulation of the actually obtained fluid in a wellbore interval isolated by the dual-packer module before the actually obtained fluid is drawn into the downhole sampling tool.

20. The method of claim 16 wherein the fluid theoretically obtained during the theoretical sampling operation and the fluid actually obtained during the actual sampling operation comprise two immiscible fluids.

* * * * *